(12) United States Patent
Thompson-Nauman et al.

(10) Patent No.: US 9,717,898 B2
(45) Date of Patent: Aug. 1, 2017

(54) SYSTEMS AND METHODS FOR IMPLANTING A MEDICAL ELECTRICAL LEAD

(71) Applicant: Medtronic, Inc., Minneapolis, MN (US)

(72) Inventors: Amy E. Thompson-Nauman, Ham Lake, MN (US); Melissa G. T. Christie, Andover, MN (US); Noah D. Barka, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

(21) Appl. No.: 14/257,549

(22) Filed: Apr. 21, 2014

(65) Prior Publication Data
US 2014/0330248 A1    Nov. 6, 2014

Related U.S. Application Data

(60) Provisional application No. 61/820,014, filed on May 6, 2013.

(51) Int. Cl.
*A61N 1/05*  (2006.01)
*A61M 5/14*  (2006.01)
(Continued)

(52) U.S. Cl.
CPC ............ *A61N 1/05* (2013.01); *A61B 17/3468* (2013.01); *A61M 5/14* (2013.01); *A61B 17/3462* (2013.01); *A61B 17/3494* (2013.01); *A61B 2017/00243* (2013.01); *A61B 2017/00331* (2013.01); *A61B 2017/00455* (2013.01);
(Continued)

(58) Field of Classification Search
CPC ...... A61B 17/3468; A61B 2017/00243; A61B 2017/00331; A61B 2017/0034; A61N 1/05
See application file for complete search history.

(56) References Cited

U.S. PATENT DOCUMENTS 4,030,509 A   6/1977  Heilman et al.
4,146,037 A   3/1979  Flynn et al.
(Continued)

FOREIGN PATENT DOCUMENTS

WO   0123035 A1    4/2001
WO   2004073506 A2  9/2004

OTHER PUBLICATIONS

Obadia, et al., "New Approach for Implantation of Automatic Defibrillators Using Videothoracoscopy", Journal Ann Cardiol Angeiol (Paris); Sep. 1994; 43 (7) Abstract Only, 1 page.
(Continued)

*Primary Examiner* — Kevin C Sirmons
*Assistant Examiner* — Deanna K Hall

(57) ABSTRACT

Implant tools and techniques for implantation of a medical lead, catheter or other implantable component are provided. The implant tools and techniques are particularly useful in implanting medical electrical leads in implant locations such as substernal spaces or subcutaneous locations. The implant tools include a sheath coupled to a sealing device. The sheath includes a continuous lumen that is in fluid communication with a passage of the sealing device. The lead is advanced through the passage and the lumen for placement of the distal end of the lead at the implant location.

15 Claims, 12 Drawing Sheets

(51) Int. Cl.
  *A61B 17/34* (2006.01)
  *A61B 17/00* (2006.01)
  *A61B 17/32* (2006.01)

(52) U.S. Cl.
  CPC . *A61B 2017/320056* (2013.01); *A61N 1/0504* (2013.01); *A61N 1/0563* (2013.01)

(56) References Cited

U.S. PATENT DOCUMENTS

| | | |
|---|---|---|
| 4,270,549 A | 6/1981 | Heilman |
| 4,280,510 A | 7/1981 | O'Neill |
| 4,291,707 A | 9/1981 | Heilman et al. |
| 4,437,475 A | 3/1984 | White |
| 4,512,351 A | 4/1985 | Pohndorf |
| 4,538,624 A | 9/1985 | Tarjan |
| 4,552,157 A | 11/1985 | Littleford |
| 4,664,113 A | 5/1987 | Frisbie et al. |
| 4,765,341 A | 8/1988 | Mower et al. |
| 4,832,687 A | 5/1989 | Smith, III |
| 5,036,854 A | 8/1991 | Schollmeyer et al. |
| 5,125,904 A | 6/1992 | Lee |
| 5,176,135 A | 1/1993 | Fain et al. |
| 5,255,691 A | 10/1993 | Otten |
| 5,300,106 A | 4/1994 | Dahl et al. |
| 5,312,355 A | 5/1994 | Lee |
| 5,441,504 A | 8/1995 | Pohndorf et al. |
| 5,456,699 A | 10/1995 | Armstrong |
| 5,509,924 A | 4/1996 | Paspa et al. |
| 5,613,953 A | 3/1997 | Pohndorf |
| 5,690,648 A | 11/1997 | Fogarty et al. |
| 5,782,239 A | 7/1998 | Webster, Jr. |
| 5,944,732 A | 8/1999 | Raulerson et al. |
| 5,951,518 A | 9/1999 | Licata et al. |
| 6,032,079 A | 2/2000 | KenKnight et al. |
| 6,104,957 A | 8/2000 | Alo et al. |
| 6,122,552 A | 9/2000 | Tockman et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,544,247 B1 | 4/2003 | Gardeski et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,866,044 B2 * | 3/2005 | Bardy .................. A61N 1/375 128/898 |
| 6,868,291 B1 | 3/2005 | Bonner et al. |
| 6,887,229 B1 | 5/2005 | Kurth |
| 6,890,295 B2 | 5/2005 | Michels et al. |
| 7,033,326 B1 | 4/2006 | Pianca et al. |
| 7,069,083 B2 | 6/2006 | Finch et al. |
| 7,117,039 B2 | 10/2006 | Manning et al. |
| 7,158,838 B2 | 1/2007 | Seifert et al. |
| 7,192,433 B2 | 3/2007 | Osypka et al. |
| 7,195,637 B2 | 3/2007 | Mika |
| 7,218,970 B2 | 5/2007 | Ley et al. |
| 7,229,450 B1 | 6/2007 | Chitre et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,450,997 B1 | 11/2008 | Pianca et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 * | 2/2010 | Ko .................. A61M 25/0668 606/129 |
| 7,736,330 B2 | 6/2010 | Bardy |
| 7,765,014 B2 | 7/2010 | Eversull et al. |
| 7,801,622 B2 | 9/2010 | Camps et al. |
| 7,837,671 B2 | 11/2010 | Eversull et al. |
| 7,846,088 B2 | 12/2010 | Ness |
| 7,850,610 B2 | 12/2010 | Ferek-Petric |
| 7,930,040 B1 | 4/2011 | Kelsch et al. |
| 7,983,765 B1 | 7/2011 | Doan et al. |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,260,436 B2 | 9/2012 | Gerber et al. |
| 8,280,527 B2 | 10/2012 | Eckerdal et al. |
| 8,340,779 B2 | 12/2012 | Harris et al. |
| 8,355,786 B2 | 1/2013 | Malinowski |
| 8,386,052 B2 | 2/2013 | Harris et al. |
| 8,394,079 B2 | 3/2013 | Drake et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,478,424 B2 | 7/2013 | Tronnes |
| 8,478,426 B2 | 7/2013 | Barker |
| 2002/0120294 A1 | 8/2002 | Kroll |
| 2003/0114908 A1 | 6/2003 | Flach |
| 2004/0059348 A1 | 3/2004 | Geske et al. |
| 2004/0102829 A1 | 5/2004 | Bonner et al. |
| 2004/0210293 A1 | 10/2004 | Bardy et al. |
| 2004/0236396 A1 | 11/2004 | Coe et al. |
| 2005/0049663 A1 | 3/2005 | Harris et al. |
| 2005/0131505 A1 | 6/2005 | Yokoyama |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0253181 A1 | 11/2006 | Schulman et al. |
| 2007/0023947 A1 | 2/2007 | Ludwig et al. |
| 2007/0055204 A1 | 3/2007 | Geisler et al. |
| 2007/0100409 A1 | 5/2007 | Worley et al. |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0179562 A1 | 7/2010 | Linker et al. |
| 2010/0217298 A1 | 8/2010 | Bardy |
| 2010/0217301 A1 | 8/2010 | Bardy |
| 2010/0249696 A1 | 9/2010 | Bardy |
| 2010/0262158 A1 | 10/2010 | Siegel et al. |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2013/0066331 A1 | 3/2013 | Chitre et al. |

(56) References Cited

U.S. PATENT DOCUMENTS

| | | |
|---|---|---|
| 2013/0103049 A1 | 4/2013 | Bonde |
| 2013/0158564 A1 | 6/2013 | Harris et al. |
| 2013/0238067 A1 | 9/2013 | Baudino |

OTHER PUBLICATIONS

Lemmer, "Defibrillator Patch Constriction, Letter to the Editor", The Annals of Thoracic Surgery, 1996, 1 page.
Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.
Damiano, "Implantation of Cardioverter Defibrillators in the Post - Sternotomy Patient", The Annals of Thoracic Surgery, 1992; 53: pp. 978-983.
Piccione, et al., "Erosion of Extrapericardial Implantable Cardioverter Defibrillator Patch Through the Gastic Fundus with Fistulous Tract Information", Cardiology in Review; 2006; 14, e21-e23 pages.
Vyhmeister et al., "Simple Approach for Extrapericardial Placement of Defibrillator Patches via Median Sternotomy", The Annals of Thoracic Surgery; 1994; 57: 4 pages.
Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.
Obadia et al., "Thoracoscopic Approach to Implantable Cardioverter Defibrillator Patch Electrode Implantation", Pacing and Clinical Electrophysiology; Jun. 1996; vol. 19; 6 pages.
Shapira, et al., A Simplied Method for Implantation of Automatic Cardioverter Defibrillator in Patients with Previous Cardiac Surgery, Pacing and Clinical Electrophysiology, January Part I, 1993, vol. 16; 6 pages.
Quigley et al., "Migration of an Automatic Implantable Cardioverter-Defibrillator Patch Causing Massive Hemothorax", Journal Texas Heart Institute, Nov. 1, 1996; vol. 23, 4 pages.
Karwande et al., Bilateral Anterior Thoracotomy for Automatic Implantable Cardioverter Defibrillator Placement in Patients with Previous Sternotomy, The Annals of Thoracic Surgery; Oct. 1992; 54(4); 3 pages.
Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., Subepicardial Infarction, Myocardial Impression, and Ventricular Penetration by Sutureless Electrode and Leads, Chest; 70: 1, Jul. 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Medtronic, Inc. 6996SQ Subcutaneous, Unipolar Lead with Defibrillation Coil Electrode, Technicial Manual, 22 pages.
Medtronic, Inc. 6996T Tunneling Tool, Technical Manual, 12 pages.
Pebax Product Brochure, 14 pages and can be found on-line at http://www.pebax.com/export/sites/pebax/.content/medias/downloads/literature/pebax-product-range-brochure.pdf, 14 pages.
Cigna et al., A New Technique for Substernal Colon Transposition with a Breast Dissector: Report of 39 Cases, Journal of Plastic, Reconstructive and Aesthetic Surgery, 2006:59, 4 pages.
Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 pages.
Molina et al, "An Epicardial Subxiphoid Implantable Defibrillator Lead: Superior Effectiveness After Failure of Stndard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Baudoin et al., The Superior Epigastric Artery Does Not Pass Through Larrey's Space (Trigonum Sternocostale) Surgical Radiol Anat (2003), 25: 259-262.
Haydin et al., "Subxiphoid Approach to Epicardial Implantation of Implantable Cardioverter Defibrillators in Children", PACE, vol. 36, Aug. 2013, 5 pages.
Ganapathy et al., "Implantable Device to Monitor Cardiac Activity with Sternal Wires," Pace, vol. 37, Dec. 2014, 11 pages.
Guenther et al., "Substernal Lead Implantation: A Novel Option to Manage DFT Failure in S-ICD patients," Clinical Research Cardiology, Published On-line Oct. 2, 2014, 3 pages.
Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

\* cited by examiner

SYSTEMS AND METHODS FOR IMPLANTING A MEDICAL ELECTRICAL LEAD

CROSS-REFERENCE TO RELATED APPLICATIONS

This application claims the benefit of priority from U.S. Provisional Application No. 61/820,014, filed on May 6, 2013, the content of which is incorporated herein by reference in its entirety.

FIELD

The disclosure relates generally to implantable medical devices of the type for performing monitoring of a physiologic state and/or therapy delivery. In particular, the disclosure pertains to tools for implanting medical electrical leads for the physiologic state monitoring and/or therapy delivery.

BACKGROUND

Implantable cardiac defibrillator (ICD) systems are used to deliver high energy electrical pulses or shocks to a patient's heart to terminate life threatening arrhythmias, such ventricular fibrillation. Traditional ICD systems include a housing that encloses a pulse generator and other electronics of the ICD and is implanted subcutaneously in the chest of the patient. The housing is connected to one or more implantable medical electrical leads that are implanted within the heart.

Traditional ICD systems that utilize transvenous leads may not be the preferable ICD system for all patients. For example, in some patients, difficult vascular access precludes placement of transvenous leads. As another example, children and other younger patients may also be candidates for non-transvenous ICD systems. Moreover, transvenous leads may become fibrosed in the heart over time, making lead revision and extraction procedures challenging.

A subcutaneous ICD system may be preferred for some patients. A subcutaneous ICD system includes a lead (or leads) that are implanted subcutaneously in the patient, i.e., between the skin and the ribs and/or sternum of the patient. As such, the subcutaneous ICD may eliminate the need for transvenous leads being within the heart. A need exists for tools and methods for delivery of non-transvenous leads to implant locations other than to the heart.

SUMMARY

This disclosure, among other things, describes techniques, devices and methods for implantation of an implantable medical lead. Exemplary implantation devices comprise a sheath having a proximal end and a distal end with a lumen extending between the proximal end and the distal end, a sealing assembly coupled to the sheath, the sealing assembly having a passage therethrough that is in substantial axial alignment with the lumen, and an elongate tool configured to be disposed within the passage and the inner lumen and having a pre-biased curvature formed along a length of a body of the elongate tool, wherein the pre-biased curvature orients a distal portion of the elongate tool along a first plane that is different from a plane defined by a proximal portion of the elongate tool.

Other aspects of the disclosure include methods for implanting an implantable medical lead comprising providing a delivery system comprising a sheath having a lumen and a sealing assembly having a passage that is in fluid communication with the lumen, and an elongate tool disposed within the lumen and the passage, inserting the delivery system through an access point into the substernal space, orienting a distal portion of the delivery system towards a sternum of the patient, advancing the delivery system through the substernal space to a predetermined implant site, removing the elongate body from the lumen and the passage and inserting a lead through the passage into the lumen, and advancing the lead of the implantable medical system to position a distal end of the lead at the predetermined location.

BRIEF DESCRIPTION OF THE DRAWINGS

Various exemplary embodiments of the compositions and methods according to the invention will be described in detail, with reference to the following figures wherein.

Figure 1A:
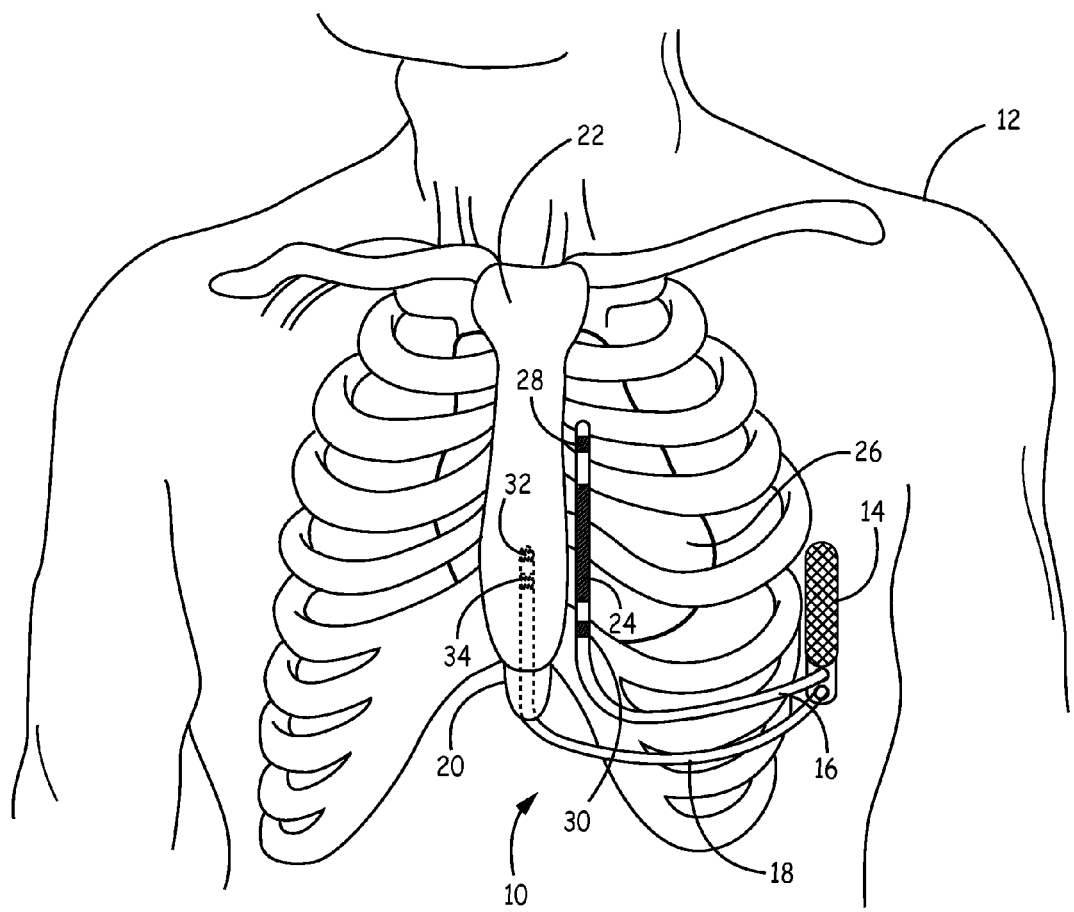
FIG. 1A is a front view of a patient implanted with implantable cardiac system.

The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

DETAILED DESCRIPTION

In this disclosure, techniques, components, assemblies, and methods for delivery of a lead into a targeted delivery site within a substernal space are described. The lead may be delivered through a surgical incision created on the skin/tissue adjacent to or below the xiphoid process (also referred to as "subxiphoid") to form an access point to the substernal space, and advancing the lead with the aid of a delivery system through which the lead is inserted into the substernal space. The access point may also be formed at the notch (not shown) that connects the xiphoid process to the sternum. In other embodiments, the substernal space may also be accessed through the manubrium.

In this disclosure, "substernal space" refers to the region defined by the undersurface between the sternum and the body cavity but not including the pericardium. In other words, the region is posterior to the sternum and anterior to the ascending aorta. The substernal space may alternatively be referred to by the terms "retrosternal space" or "mediastinum" or "infrasternal" as is known to those skilled in the art and includes the region referred to as the anterior mediastinum. The substernal space may also include the anatomical region described in Baudoin, Y. P., et al., entitled "The superior epigastric artery does not pass through Larrey's space (trigonum sternocostale)." *Surg. Radiol. Anat.* 25.3-4 (2003): 259-62 as Larrey's space. For ease of description, the term substernal space will be used in this disclosure, it being understood that the term is interchangeable with any of the other aforementioned terms.

In this disclosure, the term "extra-pericardial" space refers to region around the outer heart surface, but not within the pericardial sac/space. The region defined as the extra-pericardial space includes the gap, tissue, bone, or other anatomical features around the perimeter of, and adjacent to the pericardium.

Figure 1B:
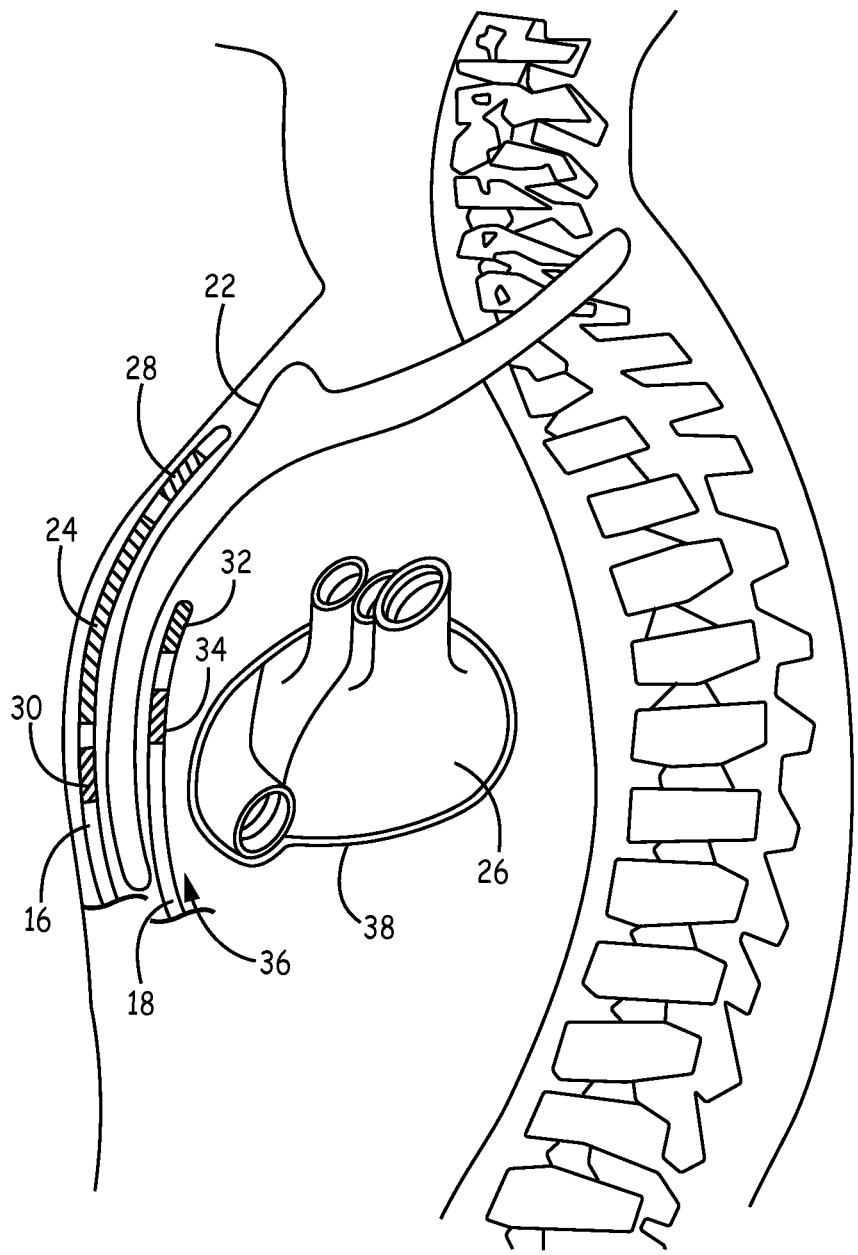
FIG. 1B is a side view the patient implanted with implantable cardiac system.
Figure 1C:
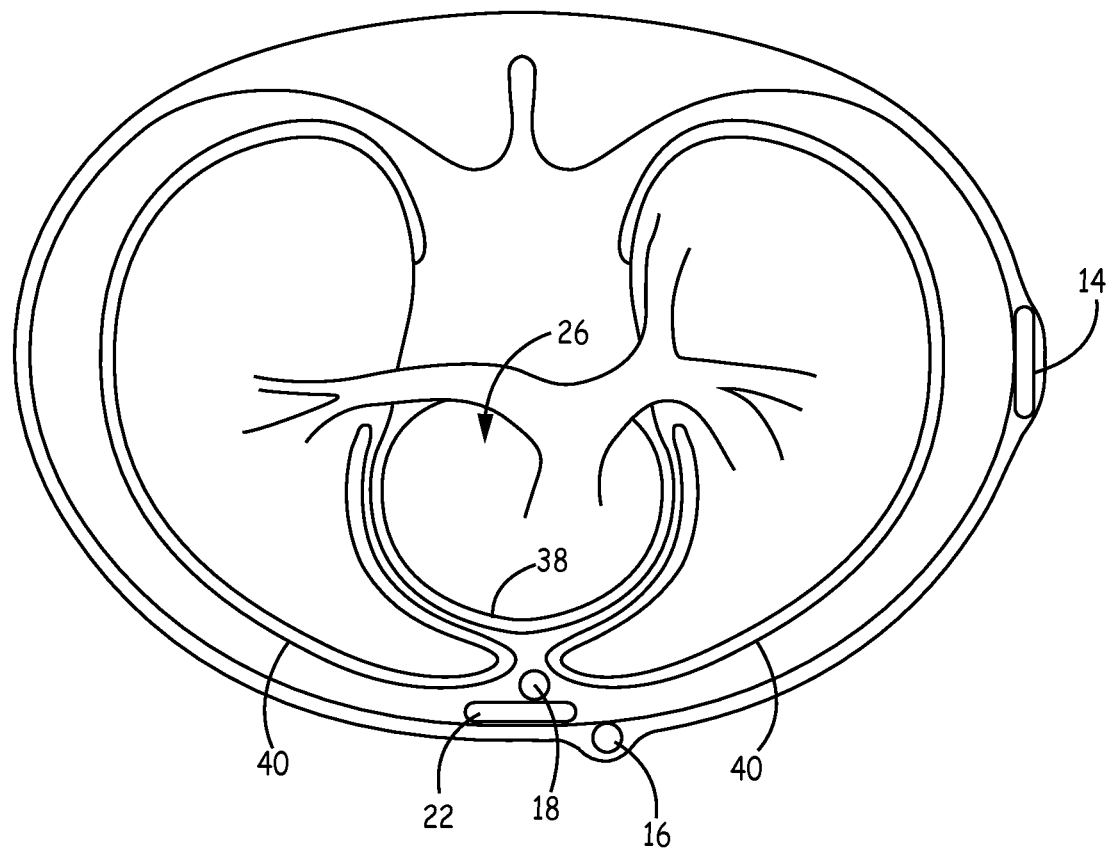
FIG. 1C is a transverse view of the patient implanted with implantable cardiac system.

FIGS. 1A-C are conceptual diagrams of a patient 12 implanted with an example implantable cardiac system 10. FIG. 1A is a front view of patient 12 implanted with implantable cardiac system 10. FIG. 1B is a side view patient 12 with implantable cardiac system 10. FIG. 1C is a transverse view of patient 12 with implantable cardiac system 10.

Implantable cardiac system 10 includes an implantable cardiac defibrillator (ICD) 14 connected to a first lead 16 and a second lead 18. The first lead 16 and the second lead 18 may be utilized to provide an electrical stimulation therapy such as pacing or defibrillation. For example, lead 16 may provide defibrillation therapy while lead 18 may provide pacing therapy, or vice versa, while in other embodiments, both lead 16 and lead 18 may provide pacing therapy or defibrillation therapy. In the example illustrated in FIGS. 1A-C ICD 14 is implanted subcutaneously on the left midaxillary of patient 12. ICD 14 may, however, be implanted at other subcutaneous locations on patient 12 as described later.

Lead 16 includes a proximal end that is connected to ICD 14 and a distal end that includes one or more electrodes. Lead 16 extends subcutaneously from ICD 14 toward xiphoid process 20. At a location near xiphoid process 20, lead 16 bends or turns and extends subcutaneously superior, substantially parallel to sternum 22. The distal end of lead 16 may be positioned near the second or third rib. However, the distal end of lead 16 may be positioned further superior or inferior depending on the location of ICD 14 and other factors. Although illustrated as being offset laterally from and extending substantially parallel to sternum 22 in the example of FIGS. 1A-C, lead 16 may be implanted over sternum 22, offset from sternum 22, but not parallel to sternum 22 (e.g., angled lateral from sternum 22 at either the proximal or distal end).

Lead 16 includes a defibrillation electrode 24, which may include an elongated coil electrode or a ribbon electrode, toward the distal end of lead 16. Lead 16 is placed such that a therapy vector between defibrillation electrode 24 and a housing or can electrode of ICD 14 is substantially across the ventricle of heart 26.

Lead 16 may also include one or more sensing electrodes, such as sensing electrodes 28 and 30, located toward the distal end of lead 16. In the example illustrated in FIGS. 1A-C, sensing electrode 28 and 30 are separated from one another by defibrillation electrode 24. ICD 14 may sense electrical activity of heart 26 via a combination of sensing vectors that include combinations of electrodes 28 and 30 and the housing or can electrode of ICD 14. For example, ICD 14 may obtain electrical signals sensed using a sensing vector between electrodes 28 and 30, obtain electrical signals sensed using a sensing vector between electrode 28 and the conductive housing or can electrode of ICD 14, obtain electrical signals sensed using a sensing vector between electrode 30 and the conductive housing or can electrode of ICD 14, or a combination thereof. In some instances, ICD 14 may even sense cardiac electrical signals using a sensing vector that includes defibrillation electrode 24.

Lead 18 includes a proximal end that is connected to ICD 14 and a distal end that includes one or more electrodes. Lead 18 extends subcutaneously from ICD 14 toward xiphoid process 20. At a location near xiphoid process 20, the lead 18 bends or turns and extends superior upward in the substernal space. In one example, lead 18 may be placed in the mediastinum 36 and, more particularly, in the anterior mediastinum. The anterior mediastinum is bounded laterally by pleurae 40, posteriorly by pericardium 38, and anteriorly by sternum 22. Lead 18 may be implanted within the mediastinum such that one or more electrodes 32 and 34 are located over a cardiac silhouette of the ventricle as observed via fluoroscopy. In the example illustrated in FIGS. 1A-C, lead 18 is located substantially centered under sternum 22. In other instances, however, lead 18 may be implanted such that it is offset laterally from the center of sternum 22. Although described herein as being implanted in the substernal space, the mediastinum, or the anterior mediastinum, lead 18 may be implanted in other extra-pericardial locations.

Lead 18 includes electrodes 32 and 34 located near a distal end of lead 18. Electrodes 32 and 34 may comprise ring electrodes, hemispherical electrodes, coil electrodes, helical electrodes, ribbon electrodes, or other types of electrodes, or combinations thereof. Electrodes 32 and 34 may be the same type of electrodes or different types of electrodes. In the example illustrated in FIGS. 1A-C electrode 32 is a hemispherical electrode and electrode 34 is a ring or coil electrode.

ICD 14 may deliver pacing pulses to heart 26 via a pacing or therapy vector that includes any combination of one or both of electrodes 32 and 34 and a housing electrode or can electrode of ICD 14. For example, ICD 14 may deliver pacing pulses using a pacing or therapy vector between electrodes 32 and 34, deliver pacing pulses using a pacing or therapy vector between electrodes 32 and the conductive housing or can electrode of ICD 14, deliver pacing pulses using a pacing or therapy vector between electrodes 34 and the conductive housing or can electrode of ICD 14, or a combination thereof. In some instances, ICD 14 may deliver pacing therapy via a therapy vector between one of electrode 32 (or electrode 34) and defibrillation electrode 24. In still further instances, ICD 14 may deliver pacing therapy via a therapy vector between one of electrode 32 (or electrode 34) and one of sensing electrodes 28 or 30. ICD 14 may generate and deliver the pacing pulses to provide anti-tachycardia pacing (ATP), bradycardia pacing, post shock pacing, or other pacing therapies or combination of pacing therapies. In this manner, ATP therapy or post shock pacing (or other pacing therapy) may be provided in an ICD system without entering the vasculature or the pericardial space, nor making intimate contact with the heart.

ICD 14 may generate and deliver pacing pulses with any of a number of amplitudes and pulse widths to capture heart 26. The pacing thresholds of heart 26 when delivering pacing pulses substernally using lead 18 may depend upon a number of factors, including location of electrodes 32 and 34, location of ICD 14, physical abnormalities of heart 26 (e.g., pericardial adhesions), or other factors. The pacing thresholds needed to capture heart 26 tend to increase with shorter pulse widths. In the case of ATP, ICD 14 may deliver pacing pulses having longer pulse widths than conventional ATP pulses to reduce the amplitude of the pacing pulses. For example, ICD 14 may be configured to deliver pacing pulses having pulse widths or durations of greater than or equal to one (1) millisecond. In another example, ICD 14 may be configured to deliver pacing pulses having pulse widths or durations of greater than or equal to ten (10) milliseconds. In a further example, ICD 14 may be configured to deliver pacing pulses having pulse widths or durations of greater than or equal to fifteen (15) milliseconds. In yet another example, ICD 14 may be configured to deliver pacing pulses having pulse widths or durations of greater than or equal to twenty (20) milliseconds. Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. Typically the lower amplitudes require longer pacing widths as illustrated in the experimental results. Reducing the amplitude of pacing pulses delivered by ICD 14 reduces the likelihood of extracardiac stimulation.

ICD 14 may sense electrical activity of heart 26 via a combination of sensing vectors that include combinations of electrodes 32 and 34 and the housing or can electrode of ICD 14. For example, ICD 14 may obtain electrical signals sensed using a sensing vector between electrodes 32 and 34, obtain electrical signals sensed using a sensing vector between electrode 32 and the conductive housing or can electrode of ICD 14, obtain electrical signals sensed using a sensing vector between electrode 34 and the conductive housing or can electrode of ICD 14, or a combination thereof. In some instances, ICD 14 may sense electrical activity of heart 26 via a sensing vector between one of electrode 32 (or electrode 34) and electrodes 24, 28 and 30 of lead 16. ICD 14 may deliver the pacing therapy as a function of the electrical signals sensed via one or more of the sensing vectors of lead 18. Alternatively or additionally, ICD 14 may deliver the pacing therapy as a function of the electrical signals sensed via the one or more of the sensing vectors of lead 16.

ICD 14 also analyzes the sensed electrical signals from one or more of the sensing vectors of lead 18 and/or one or more of the sensing vectors of lead 16 to detect tachycardia, such as ventricular tachycardia or ventricular fibrillation. In some instances, ICD 14 delivers one or more ATP therapies via the one or more pacing or therapy vectors of lead 18 in response to detecting the tachycardia in an attempt to terminate the tachycardia without delivering a defibrillation shock. If the one or more ATP therapies are not successful or it is determined that ATP therapy is not desired, ICD 14 may deliver one or more defibrillation shocks via defibrillation electrode 24 of lead 16.

The configuration described above in FIGS. 1A-1C is directed to providing ventricular pacing via lead 18. In situations in which atrial pacing is desired in addition to or instead of ventricular pacing, lead 18 may be positioned further superior. A pacing lead configured to deliver pacing pulses to both the atrium and ventricle may have more electrodes. For example, the pacing lead may have one or more electrodes located over a cardiac silhouette of the atrium as observed via fluoroscopy and one or more electrodes located over a cardiac silhouette of the ventricle as observed via fluoroscopy. A pacing lead configured to deliver pacing pulses to only the atrium may, for example, have one or more electrodes located over a cardiac silhouette of the atrium as observed via fluoroscopy. In some instances, two substernal pacing leads may be utilized with one being an atrial pacing lead implanted such that the electrodes are located over a cardiac silhouette of the atrium as observed via fluoroscopy and the other being a ventricle pacing lead being implanted such that the electrodes are located over a cardiac silhouette of the ventricle as observed via fluoroscopy ICD 14 may include a housing that forms a hermetic seal that protects components of ICD 14. The housing of ICD 14 may be formed of a conductive material, such as titanium. ICD 14 may also include a connector assembly (also referred to as a connector block or header) that includes electrical feedthroughs through which electrical connections are made between conductors within leads 16 and 18 and electronic components included within the housing. As will be described in further detail herein, housing may house one or more processors, memories, transmitters, receivers, sensors, sensing circuitry, therapy circuitry and other appropriate components. Housing 34 is configured to be implanted in a patient, such as patient 12.

Leads 16 and 18 include a lead body that includes one or more electrodes located near the distal lead end or elsewhere along the length of the lead body. The lead bodies of leads 16 and 18 also contain one or more elongated electrical conductors (not illustrated) that extend through the lead body from the connector assembly of ICD 14 provided at a proximal lead end to one or more electrodes of leads 16 and 18. The lead bodies of leads 16 and 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of leads 16 and 18 may be coupled to one or more of electrodes 24, 28, 30, 32, and 34. In one example, each of electrodes 24, 28, 30, 32, and 34 is electrically coupled to a respective conductor within its associated lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, 30, 32, and 34 and transmit sensed electrical signals from one or more of electrodes 24, 28, 30, 32, and 34 to the sensing module within ICD 14.

The examples illustrated in FIGS. 1A-C are exemplary in nature and should not be considered limiting of the techniques described in this disclosure. In other examples, ICD 14, lead 16, and lead 18 may be implanted at other locations. For example, ICD 14 may be implanted in a subcutaneous pocket in the right chest. In this example, lead 16 may be extend subcutaneously from the device toward the manubrium of the sternum and bend or turn and extend subcutaneously inferiorly from the manubrium of the sternum, substantially parallel with the sternum and lead 18 may extend subcutaneously from the device toward the manubrium of the sternum to the desired location and bend or turn and extend substernally inferiorly from the manubrium of the sternum to the desired location.

In the example illustrated in FIGS. 1A-C, system 10 is an ICD system that provides pacing therapy. However, these techniques may be applicable to other cardiac systems, including cardiac resynchronization therapy defibrillator (CRT-D) systems, cardioverter systems, or combinations thereof.

In addition, it should be noted that system 10 may not be limited to treatment of a human patient. In alternative examples, system 10 may be implemented in non-human patients, e.g., primates, canines, equines, pigs, bovines, ovines, and felines. These other animals may undergo clinical or research therapies that may benefit from the subject matter of this disclosure.

Figure 2:
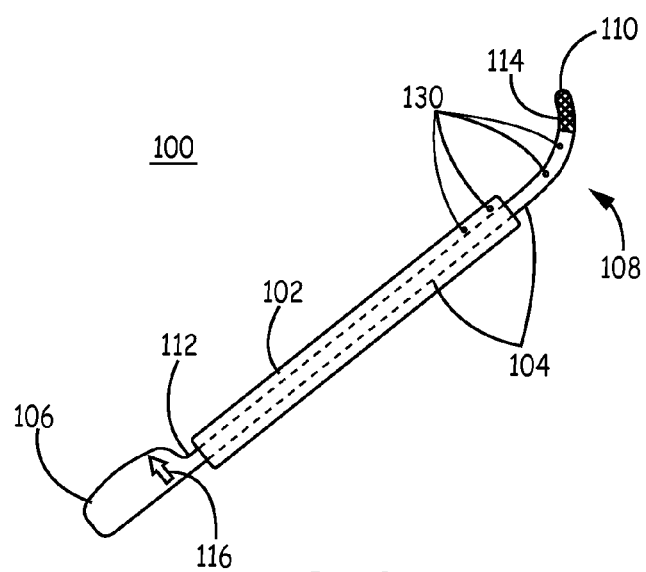
FIG. 2 depicts a perspective view of an embodiment of a delivery system for implanting a medical electrical lead.
Figure 3A:
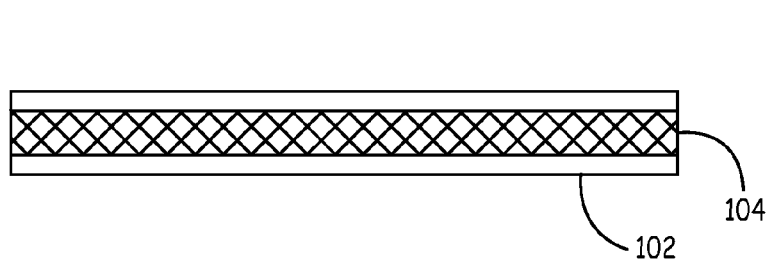
FIG. 3A depicts a side cross-sectional view of an embodiment of a delivery system for implanting a medical electrical lead.
Figure 3B:
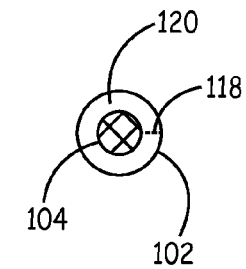
FIG. 3B shows a transverse sectional view of an embodiment of a delivery system for implanting a medical electrical lead.

FIGS. 2, 3A and 3B illustrate an embodiment of a delivery system 100 for implanting a medical electrical lead in a substernal space of a patient. The delivery system 100 may be utilized to create a pathway through the body of patient 12 to access an implant location within the substernal space. The delivery system 100 will be discussed in conjunction with FIGS. 2, 3A, and 3B, where FIG. 2 depicts a perspective view, FIG. 3A depicts a side cross-sectional view, and FIG. 3B shows a transverse sectional view.

The delivery system 100 includes a sheath 102, an elongate tool 104 and a handle 106. The sheath 102 includes a continuous lumen through which the elongate tool 104 is disposed. The continuous lumen may extend between openings at a proximal end and a distal end of the sheath 102 such that, in use, the sheath 102 is slidingly-disposed over the elongate tool 104 during axial advancement of the elongate tool 104 through patient 12 to facilitate an implant procedure.

In some embodiments, the sheath 102 may include a slit segment 118 that is formed proximate to the proximal end. The slit segment 118 may extend partially through or entirely along a length of the wall of sheath 102. For example, the slit segment 118 may be formed as perforations that extend from the inner to outer surface along the side wall of sheath 102. The slit segment 118 facilitates the slitting of the sheath 102 during the implant procedure. In use, the lead 18 will be advanced to the target site via the lumen of sheath 102. After placement of the lead 18, the sheath 102 may be separated from the lead so as to withdraw the sheath 102 from the patient 12 by slitting the side walls of the sheath 102 at the slit segment 118.

The inventors of the present disclosure have discovered that it may be desirable to implant the lead 18 such that it overlies the cardiac silhouette of the heart 26 as visualized through an imaging technique for effective therapy delivery by the lead 18. Yet, it may be desirable not to place the lead 18 in direct contact with the heart tissue. Therefore, the present disclosure addresses techniques for implanting the lead 18 in the substernal space underneath the sternum.

Accordingly, one embodiment of the elongate tool 104 includes a pre-biased curvature 108 that is formed along a length of the body of elongate tool 104 proximate to a distal end 110 of the elongate tool. As shown in FIG. 2, the pre-biased curvature 108 is configured such that the segment of the elongate body 104 adjacent to the distal end 110 is curved to orient the distal portion in a non-parallel plane relative to the plane defined by the proximal portion. The angle of curvature of the pre-biased curvature is predicated on orienting the section of the elongate tool 104 that is proximal to distal end 110 at an angle that is substantially perpendicular to the sternum of patient 12 while the rest of the elongate tool 104 is generally parallel to the sternum of patient 12. For example, the pre-biased curvature 108 is configured having a bend that orients the distal end 110 at an angle that is greater than 5 degrees relative to a first plane, with the first plane being defined along a central axis of the proximal portion of the elongate tool 104.

The distal end 110 is configured to provide a tactile signal in response to contact with tissue, bone or other anatomical features along a pathway from the access point into the substernal space of patient 12 to a desired implant location. For example, the pre-biased curvature 108 may be oriented such that the distal end 110 is placed in contact with the sternum, or more particularly the sternebrae. Continuing with the example, the distal end 110 contacts the various bones along the ribcage or at the fusion point between the ribs and the sternum or with the sternum itself as the elongate tool 104 is advanced during the implantation. Responsive to the contact between the elongate tool 104 and the patient 12, distal end 110 creates a tactile signal that provides an indication of the position of the distal end 110 relative to the patient 12.

An additional benefit of the pre-biased curvature 108 is that it positions the distal end 110 away from the body cavity and the organs underneath the sternum by orienting the distal end 110 towards the sternum during navigation of the elongate tool with the substernal space.

Sheath 102 may be formed from a pliable material such as bio-compatible plastic including polyaryletheretherketone (PEEK) thermoplastic, PARYLENE® polyxylylene polymers, or other suitable polymer material. The elongate tool 104 may be formed from a rigid material such as a metal including, titanium or stainless steel. In other embodiments, the elongate tool 104 material is a bio-compatible rigid material such, for example, as TECOTHANE® thermoplastic polyurethanes that may have elastic "memory" properties.

The handle 106 facilitates maneuvering of the elongate tool 104. As such, the handle 106 is coupled to the proximal end 112 of the elongate tool 104. The handle 106 may be formed from materials that are similar to those of the elongate tool 104 or from a dissimilar material. Handle 106 further includes a directional indicator 116 that provides an indication of the orientation of the pre-biased curvature 108 of the distal end 110. As will be discussed below, the handle 106 may alternatively be formed in a predefined shape, such that the shape of the handle will provide an indication of the orientation of the pre-biased curvature 108.

The directional indicator 116 provides a visual indicator of the orientation of distal end 110 positioned within the body of patient 12 from the exterior of the patient 12. In addition, the directional indicator 116 will facilitate re-orientation of the distal end 110 during navigation of the delivery system 100 within the body of patient 12, such, for example, as the navigation to the substernal space.

The delivery system 100 may deliver a fluid through a port or an opening to tissue adjacent to the port or opening. As will be discussed below in conjunction with embodiments of FIGS. 4, 5 and 6, the fluid may be held in a reservoir of the delivery system 100, or delivered from an external reservoir through the delivery system 100.

In one embodiment, elongate tool 104 may be provided with a lumen(s) and a fluid dispersion port(s) (not shown) for passage of the fluids through the lumen to be dispensed through the opening or port along the length of the elongate tool 104. Such a lumen is configured to dispense the fluid through an opening at the distal end 110. The lumen may facilitate delivery of a fluid such as a therapeutic solution, such as antibiotics or antimicrobial agents, or any other fluid solution (e.g., a contrast solution) during an implantation procedure of a medical electrical lead into the substernal space. For example, the fluid may be a medical anesthetic substance that is delivered into the tissue adjacent to the implant pathway as the elongate tool 104 is advanced through the patient. Alternatively, or in addition, the fluid may be a contrast solution that facilitates visualization of the elongate tool 104 to verify the location of the distal end 110.

In some embodiments, a radiopaque marker element 114 may be disposed on the elongate tool 104 and/or sheath 102. In the illustrative embodiment of FIG. 2, for instance, the element 114 is depicted overlaying a segment of the distal end 110. Nevertheless, it should be understood that the element 114 may overlay or coat any other section or sections of the elongate tool 104 or may alternatively overlay the entire elongate tool 104. Element 114 may be formed from a band of radiopaque material that is coupled to the distal end 110 through any suitable mechanism. In other embodiments, the distal-most portion of the elongate tool 104 may be formed from a radiopaque material. The radiopaque material may include a compound, such as barium sulphate, that is visible through a fluoroscopic imaging procedure. In use, the marker element 114 can provide a visual depiction or image of the distal end 110.

In other embodiments, one or more mapping electrodes 130 may be positioned on the sheath 102 or the elongate tool 104. The mapping electrodes 130 may be used in conjunction with, or as a substitute for the radiopaque marker element 114 to facilitate mapping of the location of the delivery system 100 within the substernal implant location. The mapping electrodes 130 are electrically coupled to a location mapping unit such as that disclosed in U.S. Pat. No. 7,850,610 issued to Ferek-Petric, which is incorporated herein by reference in its entirety.

In one embodiment, the elongate tool 104 and sheath 102 may be sized such that the dimensions of the lumen of sheath 102 will permit insertion of elongate tool 104 and/or the lead 18 therethrough. In an example, sheath 102 may suitably be formed having a lumen having a diameter in the range of 4 French (Fr) to 12 Fr, and preferably a 10.5 Fr diameter and having a length ranging from between 6 inches and 24 inches, it being understood that the length may further be customized outside those dimensions to cater for the variation of the human anatomy from patient-to-patient. It should be appreciated that the length of the elongate tool 104 is dimensioned to be slightly longer, for example 2 inches longer, than the sheath 102. This relative difference will ensure that the distal-most portion of the tool 104, including distal end 110, is exposed distally of the distal opening of the sheath 102. For illustrative purposes, it should be appreciated that the length of the elongate tool 104 is dimensioned having a length that enables the distal end 110 of the elongate tool 104 to be positioned adjacent to the first rib within the substernal space and extend to an incision performed on the skin adjacent to the xiphoid process of patient 12, with the proximal end 112 being located external to the patient 12.

Figure 4:
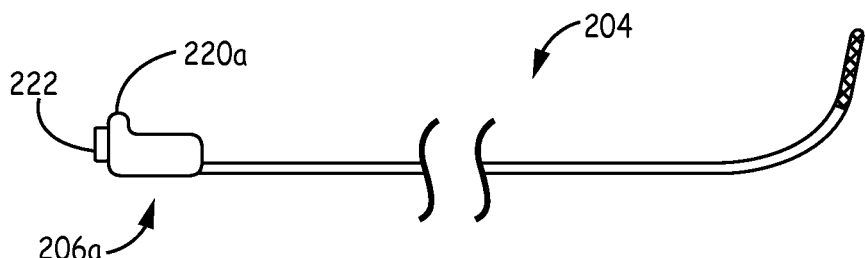
FIG. 4 depicts a perspective view of an alternative embodiment of a delivery system for implanting a medical electrical lead.
Figure 5:
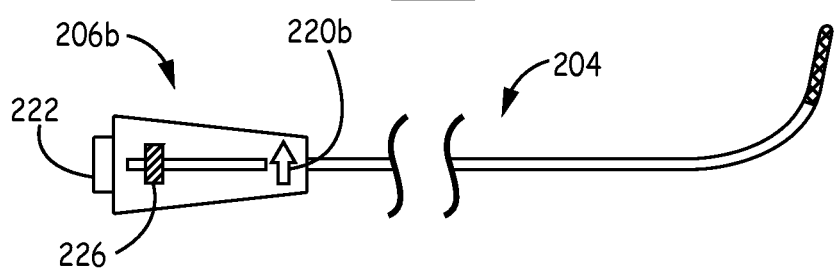
FIG. 5 depicts a perspective view of an alternative embodiment of a delivery system for implanting a medical electrical lead.
Figure 6:
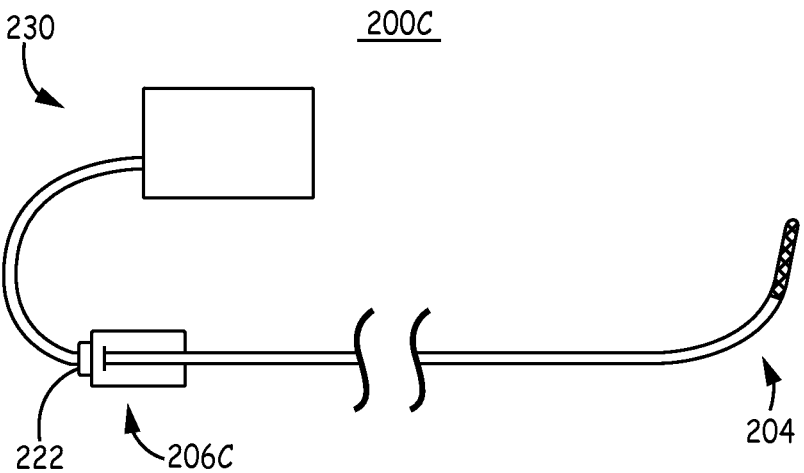
FIG. 6 depicts a perspective view of an alternative embodiment of a delivery system for implanting a medical electrical lead.
Figure 7:
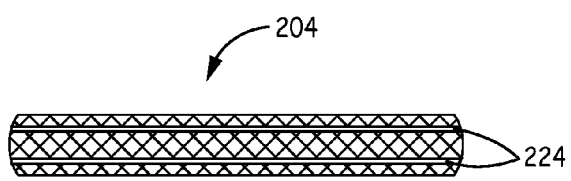
FIG. 7 illustrates a side cross-sectional view of an alternative embodiment of a portion of a delivery system.
Figure 10:
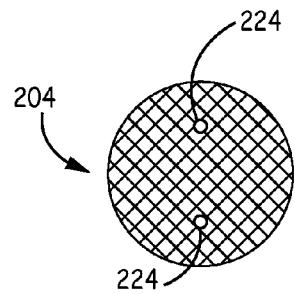
FIG. 10 illustrates a transverse cross-sectional view of an alternative embodiment of a portion of a delivery system.
Figure 8:
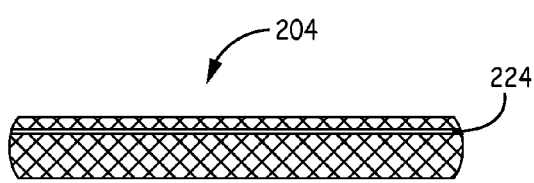
FIG. 8 illustrates a side cross-sectional view of an alternative embodiment of a portion of a delivery system.
Figure 11:
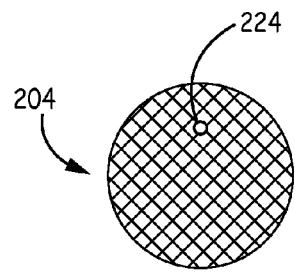
FIG. 11 illustrates a transverse cross-sectional view of an alternative embodiment of a portion of a delivery system.
Figure 9:
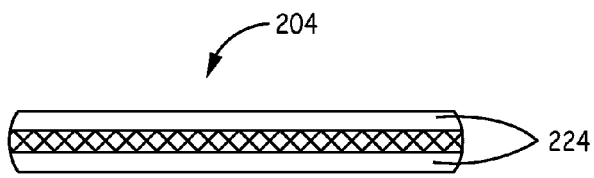
FIG. 9 illustrates a side cross-sectional view of an alternative embodiment of a portion of a delivery system.
Figure 12:
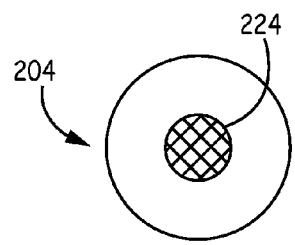
FIG. 12 illustrates a transverse cross-sectional view of an alternative embodiment of a portion of a delivery system.

FIGS. 4-6 depict alternative embodiments of delivery systems for implanting a medical electrical lead in a substernal space of a patient. FIGS. 7, 8, 9 and 10, 11, and 12 illustrate cross sectional views of alternative embodiments of an elongate tool. In particular, FIG. 7 depicts a side cross-sectional view of any one of the elongate bodies depicted in FIGS. 4-6, and FIG. 10 shows the corresponding transverse sectional view. FIG. 8 depicts a side cross-sectional view of any one of the elongate bodies depicted in FIGS. 4-6, and FIG. 11 shows the corresponding transverse sectional view. FIG. 9 depicts a side cross-sectional view of any one of the elongate bodies depicted in FIGS. 4-6, and FIG. 12 shows the corresponding transverse sectional view.

Each of the delivery systems 200a-c (collectively, "delivery system(s) 200") includes an elongate tool 204 and a handle 206a-d (collectively, "handle(s) 206"). A distal portion of the elongate tool 204 of the delivery systems 200 includes a pre-biased curvature that may correspond to the pre-biased curvature 108 described in conjunction with FIG. 2. A fluid insertion port 222 is provided on any of the handles 206a-d that may be in fluid communication with one or more fluid lumen(s) 224 disposed within the elongate tool 204. One or more fluid dispersion ports or openings (not shown) are provided in fluid communication with the fluid lumens 224 for delivery of the fluid.

The handle 206a is formed with a directional indicator 220a that is integrally formed with the handle and that can be visualized on the external surface. The handle 206a is configured to provide an indication of the orientation of the distal end of elongate tool 204. The directional indicator 220a may comprise a projection formed on a portion of the handle 206a that is shaped as a prominently visible protrusion. The directional indicator 220a such as a detent, that is directed towards a plane that is parallel to the plane of the curved portion of the distal end of the elongate tool 204.

The handle 206b illustrated in FIG. 5 includes a reservoir (not shown) that may be configured to hold a fluid for delivery through the lumen 224 of elongate tool 204. A plunger 226 may be provided to control the injection of fluid through the lumen 224.

The handle 206C illustrated in the alternative embodiment of FIG. 6 is coupled to an external reservoir that holds a fluid that is delivered through the elongate tool 204.

Figure 13:
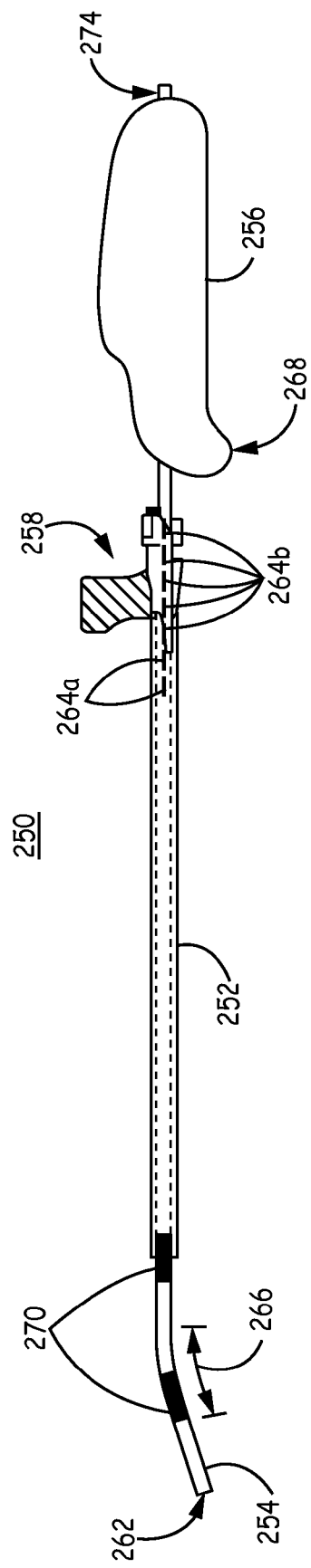
FIG. 13 depicts an alternative embodiment of a delivery system for implanting a medical electrical lead.
Figure 14:
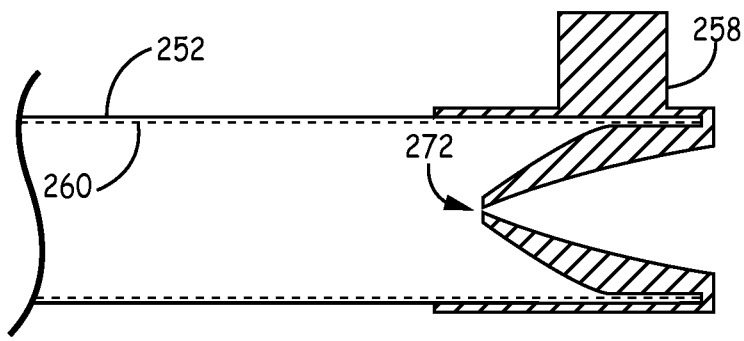
FIG. 14 depicts a partial side cross-sectional view of a portion of the delivery systems in accordance with some embodiments.
Figure 15A:
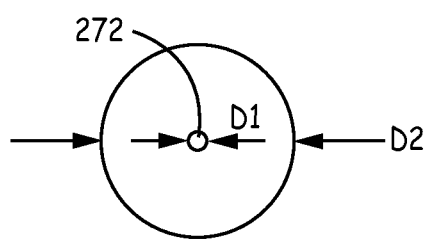
FIG. 15A shows a transverse sectional view of a portion of the delivery systems in accordance with some embodiments.
Figure 15B:
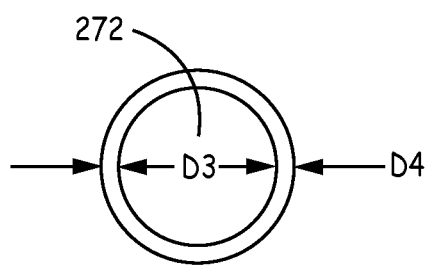
FIG. 15B shows a transverse sectional view of a portion of the delivery systems in accordance with some embodiments.

FIG. 13 depicts another embodiment of a delivery system 250 for implanting a medical electrical lead in a substernal space of a patient. The delivery system 250 includes a sheath 252, an elongate tool 254, a handle 256, and a sealing assembly 258. System 250 will be discussed in conjunction with FIGS. 14, 15A, and 15B, where FIG. 14 depicts a partial side cross-sectional view of the sheath 252 and sealing assembly 258, and FIGS. 15A and 15B show transverse sectional views of the sealing assembly 258.

Sheath 252 may be constructed with the distal terminal end having a tapered profile. Providing the tapered distal end reduces the trauma caused to patient 12 during advancement of the system 250 in an implant procedure. The sheath 252 includes a continuous lumen 260 through which the elongate tool 254 is disposed. The lumen 260 (shown in dashed lines) may extend distally from a proximal opening to a distal end 262 to facilitate axial advancement of the elongate tool 254 therethrough during an implant procedure.

A slit segment 264a may be provided along the wall of sheath 252 to enable slitting of the sheath 252 during the implant procedure. The slit segment 264a may be provided at the proximal end of the sheath 252.

In accordance with an embodiment, the elongate tool 254 is constructed with a pre-biased curvature 266 that extends proximally from the distal end 262. The pre-biased curvature 266 forms a bend at a location situated about 1 to 4 inches from the distal end 262. The angle of curvature of the pre-biased curvature may vary from between 1 degree to 20 degrees relative to an imaginary axial line formed by the proximal portion of the elongate tool, so as to orient the distal end 262 towards a different plane relative to the axial plane defined by the proximal portion of the elongate tool 254.

In use, the distal end 262 may provide a tactile signal as described in conjunction with the distal end 110 responsive to contact with tissue, bone or other anatomical features along a pathway from the access point into the substernal space of patient 12 to a desired implant location. The pre-biased curvature 266 also positions the distal end 262 away from the body cavity and the organs underneath the sternum by orienting the distal end 262 towards the sternum during navigation of the elongate tool 254 with the substernal space.

Sheath 252 may be formed from a pliable material such as bio-compatible plastic including polyaryletheretherketone (PEEK) thermoplastic, PARYLENE® polyxylylene polymers, a polyether block amide such as Pebax®, a polyolefin such as Pro-fax, or other suitable polymer material. The distal end 262 of sheath 252 may be constructed from an elastomer such as polyether block amide, or polyamide 12 and/or with a hydrophilic coating or any other material that facilitates gliding of the distal end over the elongate tool 254. The elongate tool 254 may be formed from a rigid material such as a metal including, titanium or stainless steel. In other embodiments, the material for elongate tool 254 is a bio-compatible rigid material such, for example, as TECOTHANE® thermoplastic polyurethanes that may have elastic "memory" properties.

The handle 256 is coupled to the proximal end 274 of the elongate tool 254. The handle 256 facilitates maneuvering of the elongate tool 254. Embodiments of the handle 256 may resemble the handles 106, or 206. The handle 256 is depicted having a directional indicator 268 that facilitates visualization of the orientation of distal end 262. In addition, the directional indicator 268 will facilitate re-orientation of the distal end 262 during navigation of the delivery system 250 within the body of patient 12, such, for example, as the navigation to the substernal space.

The delivery system 250 may further include a fluid lumen for delivery of a fluid through a port or an opening to tissue adjacent to the port or opening as discussed in conjunction with embodiments of FIGS. 7-12.

In other embodiments, a radiopaque marker element 270 may be disposed on the elongate tool 254. In the illustrative embodiment of FIG. 13, for instance, the element 270 is depicted overlaying two segments of the distal portion. Element 254 may be formed as a band of radiopaque material that is coupled to the elongate tool through coating or any other any suitable mechanism. The material of the radiopaque marker element 270 may include a compound, such as barium sulphate, that is visible through a fluoroscopic imaging procedure. In use, the marker element 270 can provide a visual depiction or image of the distal portion of elongate tool 254 within the patient 12. In other embodiments, the marker element 270 may be coupled to the sheath 252 instead of or in addition to being coupled to the elongate tool 254.

As described above, the elongate tool 254 and the sheath 252 may be sized such that the dimensions of the sheath 252 will permit insertion of a lead 18 therethrough.

It may be desirable to prevent air from being pushed into the body cavity of the patient 12 during the implant procedure of the lead 18. Preventing the introduction of air within the body cavity facilitates the effectiveness of therapy delivery to the patient. This may further assist in establishing the threshold parameters for the patient 12 during the implant procedure.

Accordingly, the sheath 252 is provided with the sealing assembly 258 that prevents or reduces the amount of air that is pushed into the body cavity during the implant procedure. Thus, the sealing assembly 258 may be disposed proximal to a proximal opening into the lumen 260 to provide a seal into the lumen 260 of sheath 252. The sealing assembly 258 defines a passage 272 therethrough that is substantially aligned with the lumen 260. As used herein, substantially aligned refers to the central axis of the lumen 260 and the central axis of the passage 272 being adjacent to each other such that the lumen 260 and passage 272 are in fluid communication. In addition, substantially aligned refers to the alignment of the passage 272 with a portion of the lumen 260 especially because of the dimensional differences as will be discussed below.

As shown in the illustrations of FIGS. 15A and 15B, the sealing assembly 258 is configured such that passage 272 defines a first diameter D1 prior to introduction of an accessory device such as the elongate tool 254 or lead 18, and a second diameter D2 responsive to insertion of the accessory device. Hence, the diameter D1 is less than the diameter D2. In an embodiment, the sealing assembly 258 tapers distally towards the intersection of the passage 272 with the lumen 260. For example, the passage 272 may expand up to 100% of the diameter of the lumen 260 or as little as 0.1% of the diameter of the lumen 260. The sealing assembly 258 is constructed such that the diameter D1 is tailored to accommodate passage of the accessory devices, e.g., elongate tool 254 and the lead 18, while providing an interference seal to prevent ingress of air around the outer circumference of the accessory device. In order to accommodate variations in the diameters of the accessory devices, the sealing assembly 258 is formed from materials that have the necessary elongation properties to prevent permanent deformation during insertion and passage of the accessory devices. Such a material may include a relatively soft and resilient material, for example, a liquid silicone rubber (LSR) material or a thermoplastic elastomer (TPE) material, as compared to the material that forms the sheath 252.

The sealing assembly 258 may also be formed having a slit segment 264b that extends from an exterior surface of the sidewall to the interior surface. The slit segment 264b is formed such that it is continuous with the slit segment 264a to create a continuous slit path. As has been described above, the slit segment 264b in conjunction with slit segment 264a will enable the sheath 252 to be separate from the lead 18 during an implant procedure.

Although the sealing assembly 258 is depicted being positioned proximate to the proximal end 274, it should be understood that the sealing assembly 258 may suitably be positioned anywhere along a length of the sheath 252.

Figure 16:
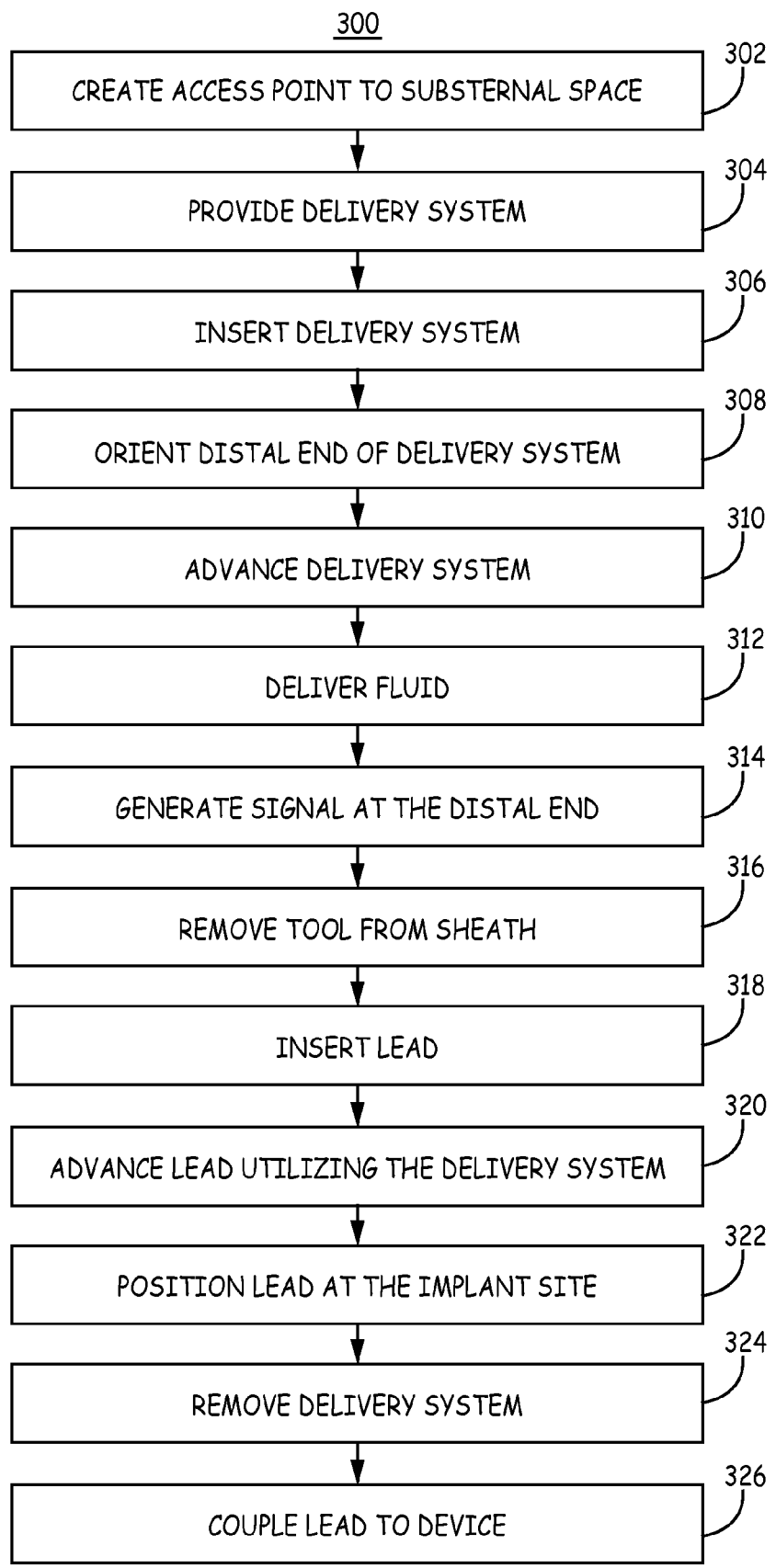
FIG. 16 is a flow chart depicting a method of implanting a lead according to an embodiment of the disclosure.
Figure 17:
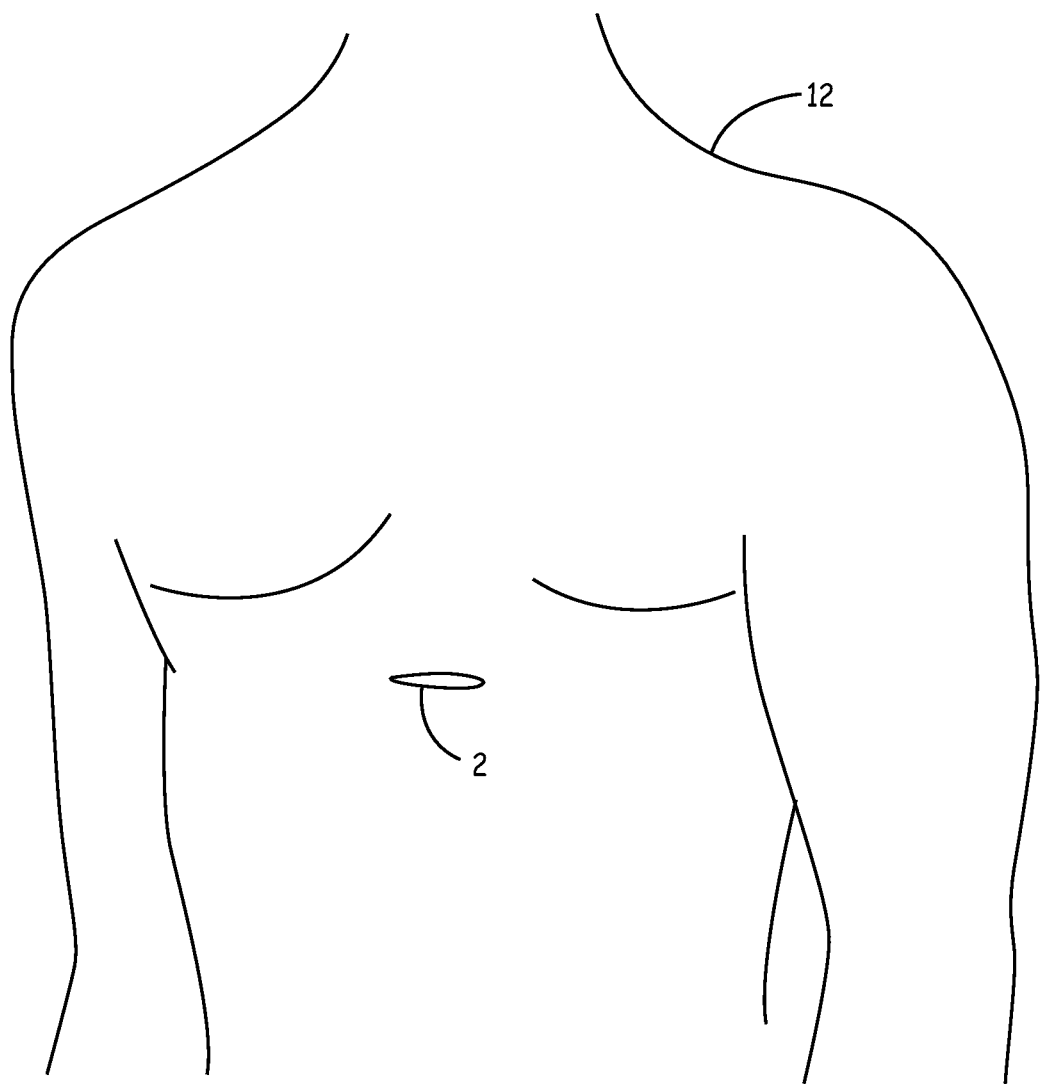
FIGS. 17-19 are partial perspective views that illustrate the method of implanting a lead of FIG. 16.
Figure 18:
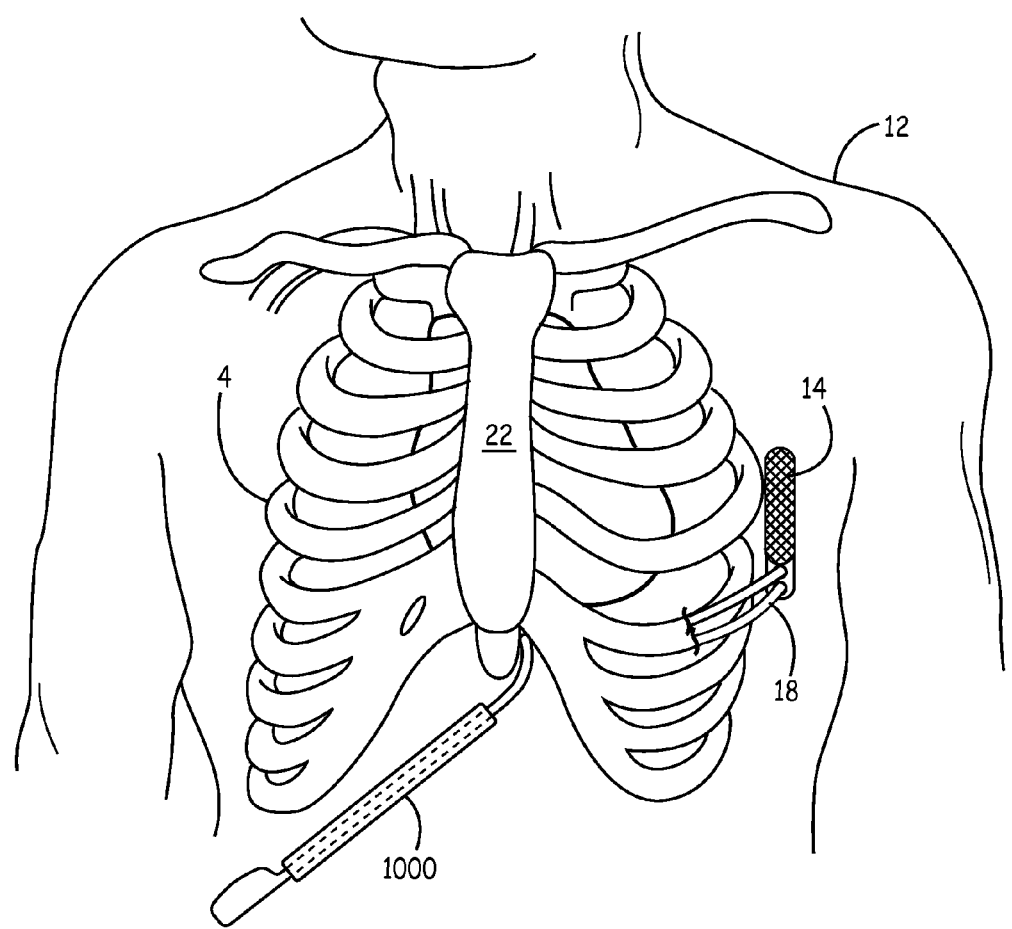
Figure 19:
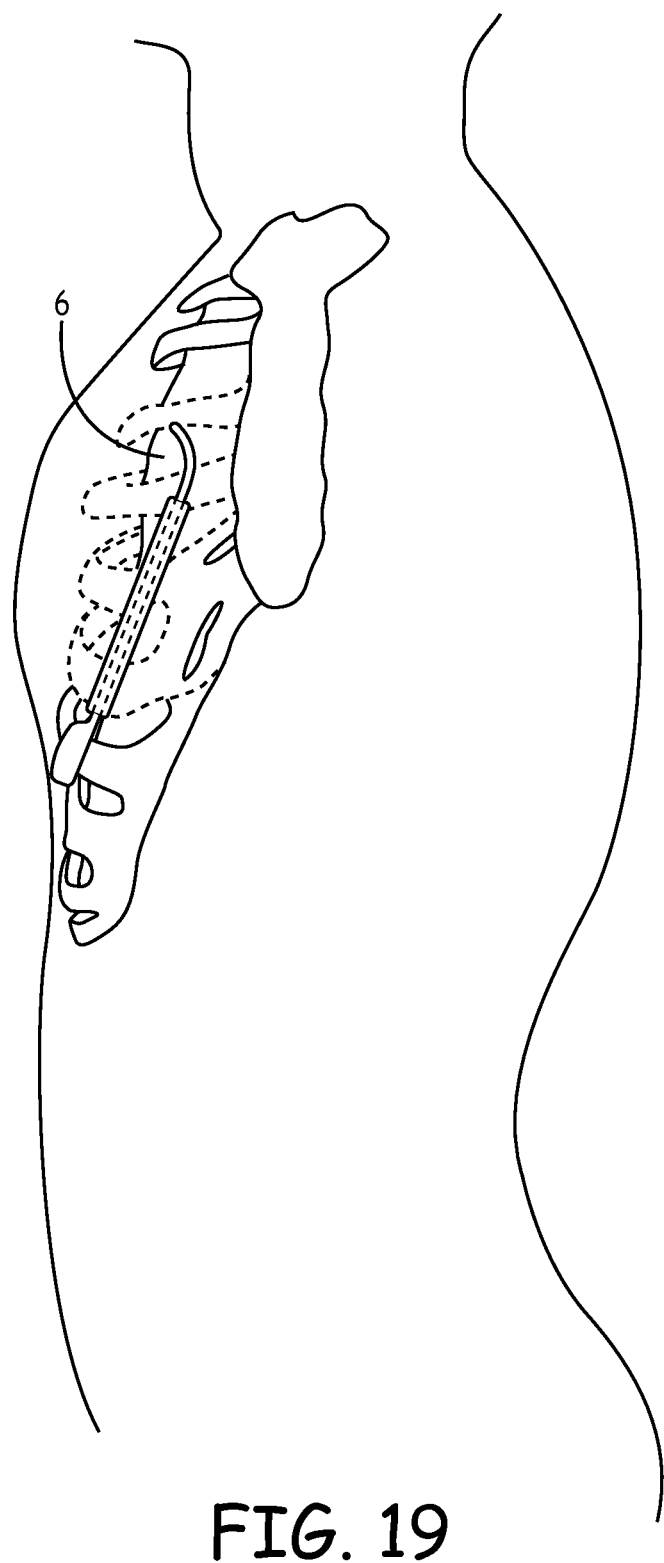

FIG. 16 is a flow chart 300 of a method of implanting a lead according to an embodiment of the present invention. FIGS. 17-19 are partial perspective views that illustrate the method 300 of implanting the lead 18 at a suitable implant location within a substernal space 6. FIGS. 18-19 depict a schematic view of the ribcage 4 of patient 12. The sternum 22 is a flat, narrow bone comprising three segments: the manubrium, the body, and the xiphoid process.

At task 302, an incision 2 is made on the skin/tissue adjacent to or below the xiphoid process (also referred to as "subxiphoid") to form an access point sized for passage of a delivery system and/or a lead (FIG. 17) to the substernal space. The access point may also be formed at the notch (not shown) that connects the xiphoid process to the sternum. In other embodiments, the substernal space may also be accessed through the manubrium. FIG. 17 illustrates the exemplary anterior or pectoral incision 2 on patient 12. The incision location provides access to the substernal space 6 underneath the ribcage 4 and is sized to allow insertion of a delivery system for navigation of the lead. The lead e.g., lead 18, may be coupled to an implantable medical device 14 that is implantable or implanted in a subcutaneous location. As such a portion of the lead 18 may be tunneled through subcutaneous tissue from the device 14 to the incision location.

A delivery system 1000 is provided for facilitating the lead implant (304). The delivery system 1000 may be embodied as any of the aforementioned delivery systems 100, 200, 250, or combinations thereof, described in conjunction with FIGS. 2-15B that include a sheath, an elongate tool, a catheter and optionally a sealing assembly. The delivery system 1000 will be provided with the elongate tool being disposed within the lumen of the sheath.

At task 306, delivery system 1000 is inserted through the incision. As described above, the exemplary delivery systems include an elongated body having a pre-biased curvature at the distal end. At task 308, the curved distal portion is oriented such that the distal end is pointed towards the sternum (FIG. 18). A directional indicator on the handle of the delivery system may be utilized to assist in placement or to confirm the proper orientation of the distal end. The directional indicator may resemble any one of those described in conjunction with the preceding figures.

At task 310, the elongated body of the delivery system is advanced within the substernal space underneath the sternum in a generally axial direction from the xiphoid process towards the jugular notch. During the advancing of the delivery system, the distal end is navigated in direct contact or close proximity with the sternum. In some embodiments, a fluid may be delivered during the advancing of the delivery system into the substernal space at task 312. For example, the delivery system may deliver an analgesic agent or a contrast solution or any other suitable fluid. Optionally, a signal is generated that is indicative of the location of the distal end of the delivery system (314). The signal may be a tactile signal such as a sensation or sound that is generated in response to the interaction of the distal end with various segments of the sternum or ribs of the ribcage connected to the sternum. Alternatively, or in addition, an imaging procedure may be performed to obtain an image of a segment of the delivery system. To that end, the radiopaque marker elements described above may be utilized in conjunction with fluoroscopy during the advancing of the delivery system 1000 to obtain a visual indication of the directional orientation of the distal portion of the delivery system within the patient. With the aid of the signal(s), the delivery system is navigated such that a distal portion is positioned at a target implant location of the distal end of the lead (FIG. 19).

Upon confirmation that the delivery system has been positioned at the appropriate location, the elongate tool is then removed from the sheath (316). Subsequent to withdrawing the elongate tool from the lumen of the sheath, the lead is then advanced through the body along the length of the lumen of the sheath (318).

It is during this exchange of the elongate tool with the lead body that potential air can be trapped in the tubing and pushed into the body cavity of the patient in the substernal space 6. As such, a delivery system such as that disclosed in FIGS. 14-15B may be utilized in accordance with some embodiments of the method. The sealing mechanism of such a delivery system will seal the distal opening of the sheath to prevent air from filling the lumen. When such a catheter is used, advancing of the lead into the sheath will not push air (or will push only a minimal amount of air) into the substernal space 6.

At task 320, the lead is advanced to the implant location through the delivery system. In one embodiment, the elongated body of the delivery system may be retracted from the sheath, leaving the sheath positioned within the substernal space. In other embodiments, the delivery system may have a lumen for insertion of the lead through the lumen. The lead may be preloaded within the lumen of the delivery system, in some examples, prior to insertion of the delivery system into the substernal space. At task 322, the lead is positioned at the appropriate implant location. In some embodiments, the positioning may include orienting the electrodes to provide a targeted stimulation therapy and/or fixation of the lead to the tissue at the implant site.

At task 324, the sheath is withdrawn from the patient 12 and the lead remains within the substernal space. In accordance with some embodiments, a slittable sheath such as those described above may be utilized. Slitting of the sheath may be performed in accordance with conventional techniques, for example, utilizing a slitting tool. The slittable sheath facilitates withdrawal of the sheath by separating the body of the sheath from the lead to ensure that the lead placement is not impacted as the sheath is pulled distally away from the incision 2. At task 326, the lead may be coupled to a stimulation pulse generator, such as ICD 14. In other embodiments the lead may be tunneled from the access point to the ICD 14 that is positioned subcutaneously on the left midaxillary of patient 12.

As described herein, delivery systems in accordance with various embodiments are provided that facilitate implantation of a lead in the substernal space. In alternative implementations, the delivery systems may be utilized for delivery of a lead in locations other than the substernal space including but not limited to the aforementioned extra-pericardial space.

Various examples have been described. It is contemplated that the features described in the different embodiments may be combined to create additional embodiments. All such disclosed and other examples are within the scope of the following claims.

What is claimed is:

1. A method of delivering an implantable medical system, comprising:
providing a delivery system comprising a sheath having a lumen and a sealing assembly having a passage that is in fluid communication with the lumen, and an elongate tool disposed within the lumen and the passage;
creating an access point into a substernal space of a patient;
inserting the delivery system through the access point into the substernal space;
orienting a distal portion of the delivery system towards a sternum of the patient;
advancing the delivery system through the substernal space to a predetermined implant site;
generating with the distal portion a signal indicative of a location of the distal portion relative to the sternum during the task of advancing;
removing the elongate tool from the lumen and the passage and inserting a lead through the passage into the lumen;
advancing the lead of the implantable medical system to position a distal end of the lead at the predetermined location; and
positioning an electrode coupled to the distal end of the lead in a predetermined orientation within the substernal space.

2. The method of delivering the implantable medical system of claim 1, wherein the elongate tool is formed having a distal terminal end and a distal portion that is curved to orient the distal terminal end of the elongate tool towards the sternum.

3. The method of delivering the implantable medical system of claim 1, further comprising obtaining an indication of a location of the distal portion of the delivery system relative to the substernal space during the task of advancing the delivery system.

4. The method of delivering the implantable medical system of claim 3, wherein obtaining the indication comprises obtaining a fluoro image of a section of the delivery system.

5. The method of delivering the implantable medical system of claim 1, further comprising delivering a fluid to the substernal space through the delivery system during the advancing of the delivery system.

6. The method of delivering the implantable medical system of claim 5, wherein the delivered fluid is one of a fluoro-visible media, a therapeutic fluid, and an analgesic agent.

7. The method of delivering the implantable medical system of claim 5, wherein the delivery system comprises an elongate tool having a fluid lumen for delivery of the fluid.

8. The method of delivering the implantable medical system of claim 1, further comprising obtaining an indication of the orientation of the distal portion of the delivery system relative to the substernal space.

9. The method of delivering the implantable medical system of claim 1, further comprising retracting the elongate tool from the sheath and utilizing the lumen to advance the lead.

10. The method of delivering the implantable medical system of claim 1, wherein accessing the substernal space comprises performing an incision at a location adjacent to a xiphoid process of the patient.

11. The method of delivering the implantable medical system of claim 8, wherein the step of generating a signal indicative of a location of the distal portion of the medical system relative to the sternum comprises generating a signal indicative of a location of a distal portion of the elongated tool.

12. The method of delivering the implantable medical system of claim 1, wherein the step of generating a signal indicative of a location of the distal portion of the medical system relative to the sternum comprises generating a signal indicative of a location of a distal portion of the elongated tool.

13. A method of delivering an implantable medical system, comprising:
providing a delivery system comprising a sheath having a lumen and a sealing assembly having a passage that is in fluid communication with the lumen, and an elongate tool disposed within the lumen and the passage;
creating an access point into a substernal space of a patient;
inserting the delivery system through the access point into the substernal space;
orienting a distal portion of the delivery system towards a sternum of the patient;
advancing the delivery system through the substernal space to a predetermined implant site;
generating with the distal portion a signal indicative of a location of the distal portion relative to the sternum during the task of advancing;
removing the elongate tool from the lumen and the passage and inserting a lead through the passage into the lumen;
advancing the lead of the implantable medical system to position a distal end of the lead at the predetermined location; and
positioning an electrode coupled to the distal end of the lead in a predetermined orientation within the substernal space; and
wherein generating the signal comprises navigating the distal portion of the delivery system to be in contact with a sternum of the patient and receiving a tactile signal indicative of a relative position of the distal portion of the delivery system with respect to the sternum.

14. The method of delivering the implantable medical system of claim 13, wherein the distal portion of the delivery system includes a pre-biased curvature oriented to form a bend of the distal portion of the delivery system.

15. The method of delivering the implantable medical system of claim 13, wherein the step of generating a signal indicative of a location of the distal portion of the medical system relative to the sternum comprises generating a signal indicative of a location of a distal portion of the elongated tool.

* * * * *